United States Patent [19]

Ito et al.

[11] Patent Number: 6,120,772
[45] Date of Patent: Sep. 19, 2000

[54] ORAL DRUGS FOR TREATING AIDS PATIENTS

[75] Inventors: Hitoshi Ito, 2-3-10 Shiroyama, Tsu, Mie; Toshimitsu Sumiya, Mie, both of Japan

[73] Assignees: Hitoshi Ito; Iwade Research Institute of Mycology Co., Ltd., both of Tsu, Japan

[21] Appl. No.: 09/169,193

[22] Filed: Oct. 8, 1998

[51] Int. Cl.[7] .............................. A01N 65/00; A61K 35/78
[52] U.S. Cl. ........................................ 424/195.1; 424/489
[58] Field of Search ........................... 424/195.1; 514/54, 514/885

[56] References Cited

U.S. PATENT DOCUMENTS 5,281,577  1/1994  Koga et al. .................................. 514/2

FOREIGN PATENT DOCUMENTS 1-067195  3/1989  Japan .............................. A61K 31/17
7-258107  10/1995  Japan ............................... A23L 1/30

OTHER PUBLICATIONS

Abstract–Pub–No.: JP01067195, Iwaide Kingaku Kenkyyusho (Iwain), Nichirie Kkaku Kenkyusho (Nchk), Jul. 1997.

Abstract–Pub–No.: JP07258107, Ito H (Itohi), Iwade Kingaku Kenkyusho KK (Iwaden), Oct. 1995.

*Primary Examiner*—Thurman K. Page
*Assistant Examiner*—Isis Ghali
*Attorney, Agent, or Firm*—Majestic, Parsons, Siebert & Hsue P.C.

[57] ABSTRACT

Oral drugs for treating AIDS patients contain water-soluble mixed components contained in cultured mycelia or a culture filtrate solution of Himematsutake (*Agaricus blazei*).

7 Claims, No Drawings

ORAL DRUGS FOR TREATING AIDS PATIENTS

BACKGROUND OF THE INVENTION

This invention relates to drugs which are to be orally administered for treating AIDS patients and in particular to such drugs of which the effective components are water-soluble mixed components contained in cultured mycelia or a culture filtrate solution of Himematsutake (*Agaricus blazei*) which is a kind of mushroom belonging to the genus of Haratake (Agaricus).

It has been reported that water-soluble components contained in fruiting bodies of mushrooms have pharmacological actions. Regarding the fruiting bodies of Himematsutake, it has been reported that water-soluble acidic polysaccharides, neutral polysaccharides and protein-bound polysaccharides contained therein have an anti-tumor activity (Japanese Patent Publications Tokkai 1-67194, 1-67195 and 2-78630) and that water-soluble mixed components contained therein have the effects of ameliorating hepatic functions, as well as an anti-tumor action (Japanese Patent Publications Tokkai 2-124829, 6-128164 and 7-258107). There has been no report, however, that water-soluble mixed components contained in cultured mycelia or a culture filtrate solution of Himematsutake has any effect of ameliorating AIDS symptoms.

SUMMARY OF THE INVENTION

It is an object of this invention to provide oral drugs for treating AIDS patients, having water-soluble mixed components contained in cultured mycelia or a culture filtrate solution of Himematsutake as their effective components.

This invention is a result of a research by the present inventors in view of the aforementioned object and is based on their discovery that the ratio of CD4 lymphocytes (helpter/inducer T cells) to CD8 lymphocytes (suppressor/cytotoxic T cells) of an AIDS patient can be significantly increased and his/her p24 antigen (HIV antigen (human immuno-deficiency virus)) can be significantly reduced if water-soluble mixed components contained in cultured mycelia or a culture filtrate solution of Himematsutake is orally administered to the patient, that is, the patient's AIDS symptoms can be significantly ameliorated.

DETAILED DESCRIPTION OF THE INVENTION

This invention relates to oral drugs for ameliorating AIDS symptoms, characterized as containing water-soluble mixed components contained in cultured mycelia of Himematsutake as their effective components. This invention also relates to oral drugs for ameliorating AIDS symptoms, characterized as containing water-soluble mixed components contained in a culture filtrate solution of Himematsutake as their effective components.

Cultured mycelia and a culture filtrate solution of Himematsutake to be used according to this invention can be obtained by a solid culture method or a liquid culture method which is commonly used for culturing basidiomycetes. For the sake of convenience of operations, however, a liquid culture method is preferred. For example, hyphae of Himematsutake may be inoculated to an ordinary disinfected medium comprising carbon sources such as glucose, saccharose and maltose, nitrogen sources such as ammonium sulphate, ammonium nitrate and sodium nitrate, natural complex nutrient resources such as maltose extract and yeast extract, inorganic salt sources such as phosphates, magnesium salts and potassium salts, and small amounts of other elements, adjusted to about pH 6.0. Mycelia will grow if this is then subjected to a shaking process or a stirred aerated jar fermentor process under an aerated condition for 15–25 days at about 30° C. while preventing contamination, and cultured mycelia and a culture filtrate solution of Himematsutake can be obtained at this stage by centrifugal separation or filtration.

Since cultured mycelia contain water-soluble mixed components which are to become the effective components of this invention, they themselves, as well as products obtained therefrom by drying and pulverizing, can be used as oral drugs. It is preferable, however, to subject them to an extraction process with heated water with temperature preferably over 60° C. and more preferably over 80° C. (herein referred to simply as "hot water"), and to use the extract thus obtained as oral drugs. In this case, it is further preferable to preliminarily wash the cultured mycelia with an organic solvent or a water-containing organic solvent such as 80 volume % ethanol in order to remove the odorous and/or coloring components peculiar to cultured mycelia of Himematsutake.

Since the water-soluble mixed components serving as the effective components of this invention are believed to be relatively heavy (high molecular number) polysaccharide-protein complexes, as will be discussed below, it is preferable to further subject the extracts obtained as above to a precipitation process by using an alcohol such as ethanol in order to remove unnecessary low-molecular components from the water-soluble components of the cultured mycelia of Himematsutake and to thereby improve the degree of purity of the effective components of this invention. It is further preferable to refine such a precipitated substance by a liquid chromatographic process for chromatographic fractionation and/or a film separation process such as dialysis and ultrafiltration and to use such a refined product for oral administration.

Since the culture filtrate solution of Himematsutake, too, contains the water-soluble mixed components which are the effective components of this invention, condensed solutions obtained therefrom can also be used as oral drugs of this invention. It is preferable, however, as explained above, to subject such a solution to a precipitation process by using an alcohol such as ethanol in order to improve the degree of purity of the effective components of this invention. Similarly, it is further preferable to refine such a precipitated substance by a liquid chromatographic process for chromatographic fractionation and/or a film separation process such as dialysis and ultrafiltration and to use such a refined product for oral administration.

As will be explained in detail below, more than 40 weight % of crude protein and more than 40 weight % of sugar components are contained in a product obtained by subjecting cultured mycelia or a culture filtrate solution of Himematsutake to an extraction with hot water, a precipitation process with an alcohol, a liquid chromatographic fractionation, dialysis and freeze-drying. The main components forming the crude protein include alanine, glutamic acid, leucine, aspartic acid and proline, and the main sugar-forming components include protein bound glucan, $\beta$-glucan, $\beta$-galactoglucan and $\alpha$-glucan, all with average molecular weight greater than 10,000. From results of such analyses, it may be concluded that the water-soluble mixed components serving as the effective components of this invention are polysaccharide-protein complexes of relatively large molecular weight (that is, average molecular weight being greater than 10,000).

Such water-soluble mixed components as described above do not exhibit a fixed decomposition point or a fixed melting point. Although they carbonize under intense heating, they are extremely stable. At a room temperature, they are stable at least for three years, and no reduction in their activity is observed even if they are subjected to a sterilization treatment at 120° C. for 20 minutes. As will be explained below, they function to significantly ameliorate AIDS symptoms when orally administered to an AIDS patient and have no problems of acute toxicity or subacute toxicity.

Next, the invention is described by way of four examples.

EXAMPLE (1)

Hyphae of Himematsutake are inoculated to a sterilized liquid medium adjusted to pH 6.0 for ordinary basidiomycetes. After mycelia are grown by a shaking culture process at 28–30° C. for 25 days under an aerated condition with protection against contamination, the cultured system is centrifuged to obtain cultured mycelia and a culture filtrate solution of Himematsutake. After the cultured mycelia thus obtained are freeze-dried and pulverized, pure water (10 times in weight) is added and the system obtained by extraction with hot water in 2 hours over a boiling water bath is centrifuged to obtain an extracted liquid. After this extracted liquid is condensed under a reduced pressure to 1/10 of its volume, ethanol is added until the final ethanol concentration becomes 70 weight % to obtain an alcohol precipitate. This precipitated system is centrifuges to obtain an ethanol precipitate. This ethanol precipitate is freeze-dried and pulverized, and this pulverized product is used as oral drug for amelioration of AIDS symptoms.

EXAMPLE (2)

The ethanol precipitate obtained in Example (1) is used as the fixed phase in column chromatography with the column filled with DETA-Toyopearl gel (tradename of product produced by Toyosoda Kabushiki Kaisha). Elution is continued until the end of color identification with glucose by the phenol-sulfuric acid method to obtain an eluted fraction. After the eluted fraction is subjected to dialysis, the remainder is freeze-dried and pulverized, and this pulverized product is used as oral drug for amelioration of AIDS symptoms.

EXAMPLE (3)

After the culture filtrate solution of Example (1) is condensed under a reduced pressure until its volume becomes 1/5, ethanol is added to the condensed liquid until the final ethanol concentration becomes 70 volume % to obtain an alcohol precipitate. This precipitated system is centrifuged to obtain an ethanol precipitate. This ethanol precipitate is freeze-dried and pulverized, and this pulverized product is used as oral drug for amelioration of AIDS symptoms.

EXAMPLE (4)

The ethanol precipitate obtained in Example (3) is used as the fixed phase in column chromatography with the column filled with DETA-Toyopearl gel (tradename of product produced by Toyosoda Kabushiki Kaisha). Elution is continued until the end of color identification with glucose by the phenol-sulfuric acid method to obtain an eluted fraction. After the eluted fraction is subjected to dialysis, the remainder is freeze-dried and pulverized, and this pulverized product is used as oral drug for amelioration of AIDS symptoms.

Next, the invention is explained by way of test examples.

Mixed Component "A" was produced first by inoculating hyphae of Himematsutake (Iwade strain 101, the tradename of product by Iwade Research Institute of Mycology Co., Ltd.) to a sterilized liquid medium for ordinary basidiomycetes adjusted to pH 6.0 and by growing mycelia by shaking culture under an aerated condition of 28–30° C. for 30 days while preventing contamination. Cultured mycelia and a culture filtrate solution of Himematsutake were obtained by centrifuging the cultured system. After the cultured mycelia were freeze-dried and pulverized, pure refined water (10 times in weight) was added to the pulverized product for extraction above a water bath maintained at 90° C. for 2 hours. The extracted system was centrifuged to obtain an extracted liquid. After this extracted liquid was condensed to 1/10 of the volume under a reduced pressure, ethanol was added until the final ethanol concentration became 70 volume % to obtain an alcohol precipitate. This precipitated system was centrifuged to obtain an ethanol precipitate. This ethanol precipitate was freeze-dried and pulverized to obtain Mixed Component "A".

After the culture filtrate obtained in the preparation of Mixed Component "A" was condensed to 1/5 of the volume under a reduced pressure, ethanol was added to the condensed liquid until the final ethanol concentration became 70 volume % to obtain an alcohol precipitate. This precipitated system was centrifuged to obtain an ethanol precipitate. This ethanol precipitate was used as the fixed phase in column chromatography with a column filled with DETA-Toyopearl gel (tradename of product by Toyosoda Kabushiki Kaisha). Elution was continued until the end of color identification with glucose by the phenol-sulfuric acid method to obtain an eluted fraction. After the eluted fraction was subjected to dialysis, the remainder was freeze-dried and pulverized to obtain Mixed Component "B".

Mixed Components "A" and "B" thus obtained were orally administered to consenting patients being treated at the Bangkok General Hospital and other related hospital of Thailand. Administration took place three times a day between meals and 10 g per administration (that is, 30 g/day). The CD4 lymphocytes and CD8 lymphocytes before and after the administration, as well as the ratio CD4/CD8, were obtained and the changes in p24 antigen were also observed. Table 1 shows the results. The average decrease in the p24 antigen three months after the administration compared to before the administration was 44% for the tested patients. In Table 1, the values of CD4 and CD8 are in units of cell/$\mu$l. Table 1 clearly shows that the present invention has the merit of significantly ameliorating AIDS symptoms.

TABLE 1

| Mixed Composite | Patient | | Before | After (months) 1 | 2 | 3 |
|---|---|---|---|---|---|---|
| "A" | Male Age 46 | CD4 | 25 | 66 | 123 | 194 |
| | | CD8 | 410 | 658 | 1213 | 1337 |
| | | CD4/CD8 | 0.061 | 0.100 | 0.101 | 0.145 |
| "A" | Female Age 26 | CD4 | 110 | 290 | 355 | 412 |
| | | CD8 | 580 | 740 | 850 | 685 |
| | | CD4/CD8 | 0.190 | 0.392 | 0.418 | 0.601 |
| "A" | Male Age 24 | CD4 | 96 | 165 | 245 | 327 |
| | | CD8 | 520 | 690 | 795 | 794 |
| | | CD4/CD8 | 0.185 | 0.239 | 0.308 | 0.412 |
| "A" | Female Age 6 | CD4 | 45 | 95 | 160 | 2981 |
| | | CD8 | 430 | 710 | 860 | 1110 |
| | | CD4/CD8 | 0.105 | 0.134 | 0.186 | 0.253 |

TABLE 1-continued

| Mixed Composite | Patient | | Before | After (months) | | |
|---|---|---|---|---|---|---|
| | | | | 1 | 2 | 3 |
| "B" | Male Age 28 | CD4 | 140 | 330 | 431 | 516 |
| | | CD8 | 580 | 860 | 998 | 935 |
| | | CD4/CD8 | 0.241 | 0.384 | 0.432 | 0.552 |
| "B" | Male Age 26 | CD4 | 130 | 420 | 650 | 798 |
| | | CD8 | 540 | 950 | 1272 | 1183 |
| | | CD4/CD8 | 0.241 | 0.442 | 0.511 | 0.675 |
| "B" | Female Age 24 | CD4 | 120 | 290 | 430 | 578 |
| | | CD8 | 520 | 780 | 1010 | 976 |
| | | CD4/CD8 | 0.231 | 0.372 | 0.426 | 0.592 |

What is claimed is:

1. An oral drug for treating AIDS patients comprising water-soluble mixed components contained in cultured mycelia of Himematsutake (*Agaricus blazei*).

2. The oral drug of claim 1 wherein said mixed components are obtained by subjecting cultured mycelia of Himematsutake to an extraction process with heated water.

3. The oral drug of claim 1 wherein said mixed components are obtained by subjecting cultured mycelia of Himematsutake to an extraction process with heated water to obtain an extract and then subjecting said extract to a precipitation process with alcohol.

4. The oral drug of claim 1 wherein said mixed components are obtained by subjecting cultured mycelia of Himematsutake to an extraction process with heated water to obtain an extract, thereafter subjecting said extract to a precipitation process with alcohol to obtain a precipitate, and thereafter refining said precipitate by chromatographic fractionation and/or preparation of membranes.

5. An oral drug for amelioration of AIDS symptoms comprising water-soluble mixed components contained in a culture filtrate solution of Himematsutake (*Agaricus blazei*).

6. The oral drug of claim 5 wherein said mixed components are obtained by subjecting a culture filtrate solution of Himematsutake to a precipitation process with alcohol to obtain a precipitate.

7. The oral drug of claim 5 wherein said mixed components are obtained by subjecting a culture filtrate solution of Himematsutake to a precipitation process with alcohol to obtain a precipitate, and thereafter refining said precipitate by chromatographic fractionation and/or preparation of membranes.

* * * * *